United States Patent
Kalish

(10) Patent No.: US 6,713,250 B1
(45) Date of Patent: *Mar. 30, 2004

(54) IDENTIFICATION OF HUMAN ALLERGENS AND T-LYMPHOCYTE ANTIGENS IN VITRO

(75) Inventor: Richard S. Kalish, East Setauket, NY (US)

(73) Assignee: The Research Foundation of State University of New York, Albany, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1088 days.

(21) Appl. No.: 08/907,783

(22) Filed: Aug. 8, 1997

(51) Int. Cl.$^7$ .............................. C12Q 1/68; C12Q 1/70; G01N 33/569
(52) U.S. Cl. .................... 435/5; 435/7.22; 435/7.23; 435/7.24; 435/7.25; 435/7.31; 435/7.32; 435/7.33; 435/7.92; 435/7.94
(58) Field of Search ................... 424/9.1, 9.2; 435/5, 435/6, 7.22, 7.23, 7.24, 7.31, 7.33, 7.92, 7.94, 35, 347, 373, 7.25, 7.32

(56) References Cited

U.S. PATENT DOCUMENTS

| | | | |
|---|---|---|---|
| 4,772,469 A | 9/1988 | Kedar et al. ............. 424/195.1 |
| 5,106,746 A | 4/1992 | Ho ............................. 435/372 |
| 5,147,289 A | 9/1992 | Edelson ......................... 604/4 |
| 5,283,323 A | 2/1994 | Berzofsky et al. ........ 424/178.1 |
| 5,290,681 A | 3/1994 | Kuroda et al. ............. 435/7.23 |
| 5,383,847 A | 1/1995 | Edelson ........................... 604/6 |
| 5,529,921 A | 6/1996 | Peterson et al. ............. 435/375 |
| 5,569,585 A | 10/1996 | Goodwin et al. .............. 435/6 |

FOREIGN PATENT DOCUMENTS

| WO | WO 94/02156 | 2/1994 |
|---|---|---|
| WO | WO 95/34638 | 12/1995 |

OTHER PUBLICATIONS

Goronzy JJ et al., Jour Rheumatol. 19:573–578 1992.*
ATTC Cell and Hybridoma on–line catalog (ATTC No. CRL–1992) 1985.*
Krasteva M, et al., Clin. Exp. Allergy. 25:563–570 1996*
Del Prete GF, et al., Jour. Clin. Invest. 88:346–350 07/91.*
Li Q, et al., Arch. Toxicol. 70:414–419. 1996.*
Schwartz RH. Fundamental Immunology. WE Paul, ed., Raven Press, New York 1984.*
Rieschel RL, Occupational contact dermatitis, 349:1093–1095 Apr. 12, 1997.*
Bernhard et al., Cancer Research 55:1099–1104 (1995).
Billaud et al., Vaccine 12(1):46–55 (1994).
Degwert et al., in "Dendritic Cells in Fundamental and Clinical Immunology", Banchereau and Schmitt, Eds., vol. 2, pp. 187–189, Plenum Press, New York (1995).
Fagnoni et al., Immunology 85:467–474 (1995).
Hauser and Katz, Proc Natl Acad Sci USA 85:5625–5628 (1988).
Hauser and Katz, Immunological Reviews 117:67–84 (1990).
Kalish, J Am Acad Dermatology 32(4):640–652 (1995).
Markowicz and Engleman, J Clin Invest 85:955–961 (1990).
Mehta–Damani et al., J Immunology 153:996–1003 (1994).
Mehta–Damani et al., Eur J Immunol 25:1206–1211 (1995).
Moulon et al., Immunology 80:373–379 (1993).
Moulon et al., in "Dendritic Cells in Fundamental and Clinical Immunology", Kamperdijk et al., Eds., pp. 209–212. Plenum Press, New York (1993).
Sallusto and Lanzavecchia, J Exp Med 179:1109–1118 (1994).
Schauf et al., Cellular Immunology 137:81–87 (1991).
Steinman and Inaba, Adv Exp Med Biol 237:31–41 (1988).
Strunk et al., Blood 87(4):1292–1302 (1996).
Yokozeki et al., Int Arch Allergy Immunol 106:394–400 (1995).

* cited by examiner

Primary Examiner—David Saunders
(74) Attorney, Agent, or Firm—Rogalsky & Weyand, LLP

(57) ABSTRACT

The invention provides a method for screening a test compound for the ability of the test compound to induce a response from human naive T-cells. The method comprises admixing human naive T cells, macrophages/monocytes, immortalized B cells lacking class I and class II major histocompatibility antigens, and a test compound; and determining whether the test compound induces a response from the human naive T cells. The invention further provides a method for primary in vitro sensitization of human naive T-cells. The method comprises admixing human naive T cells, macrophages/monocytes, immortalized B cells lacking class I and class II major histocompatibility antigens, and an antigen.

46 Claims, 4 Drawing Sheets

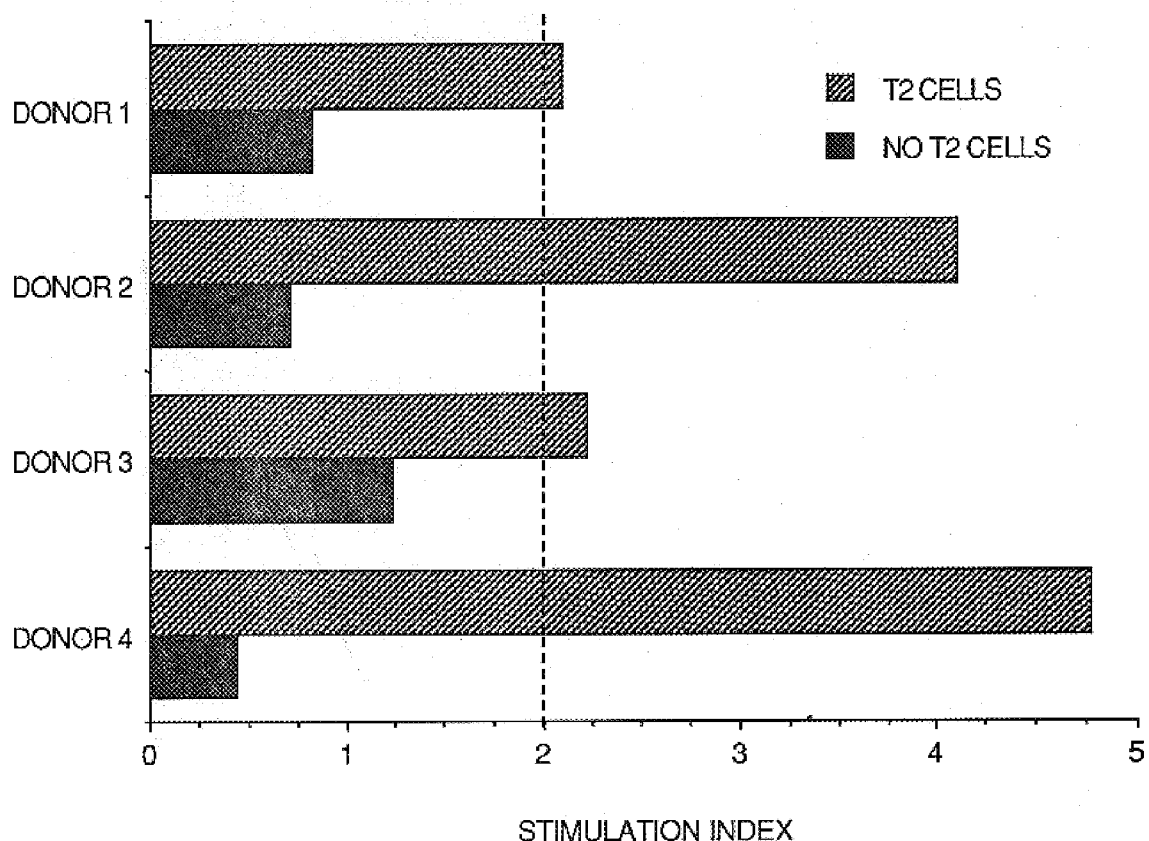

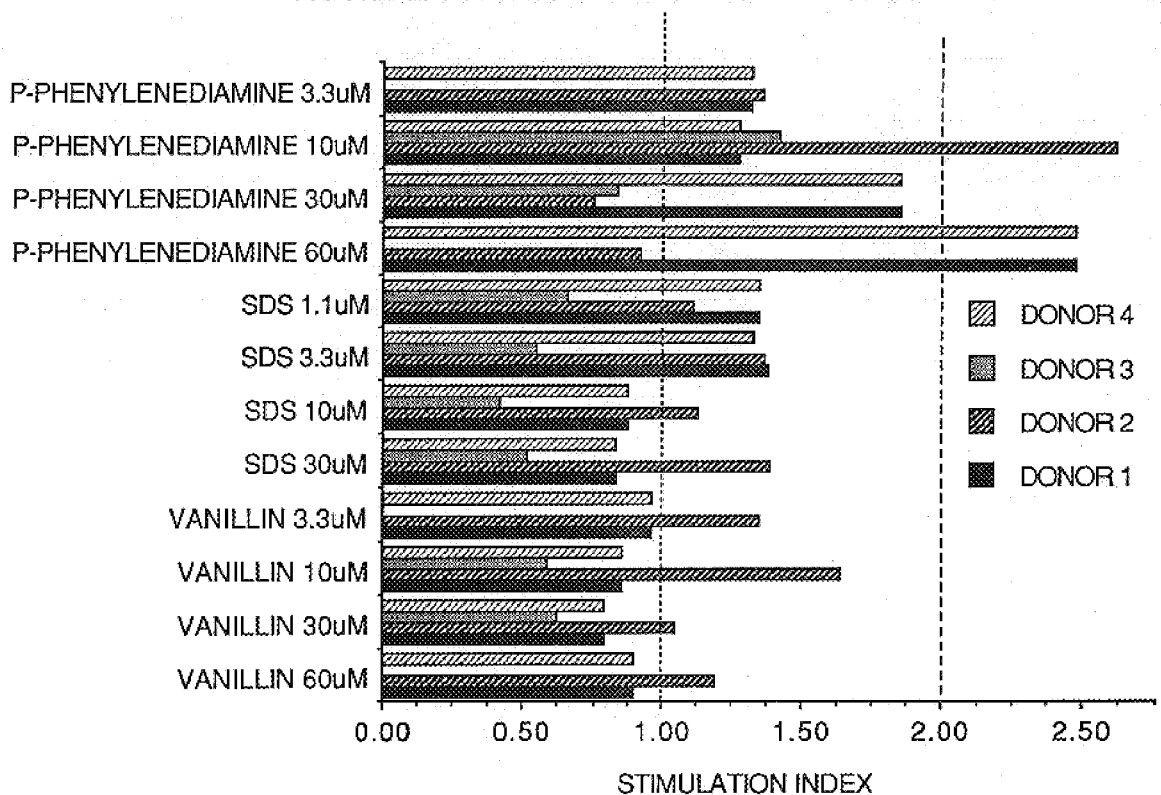

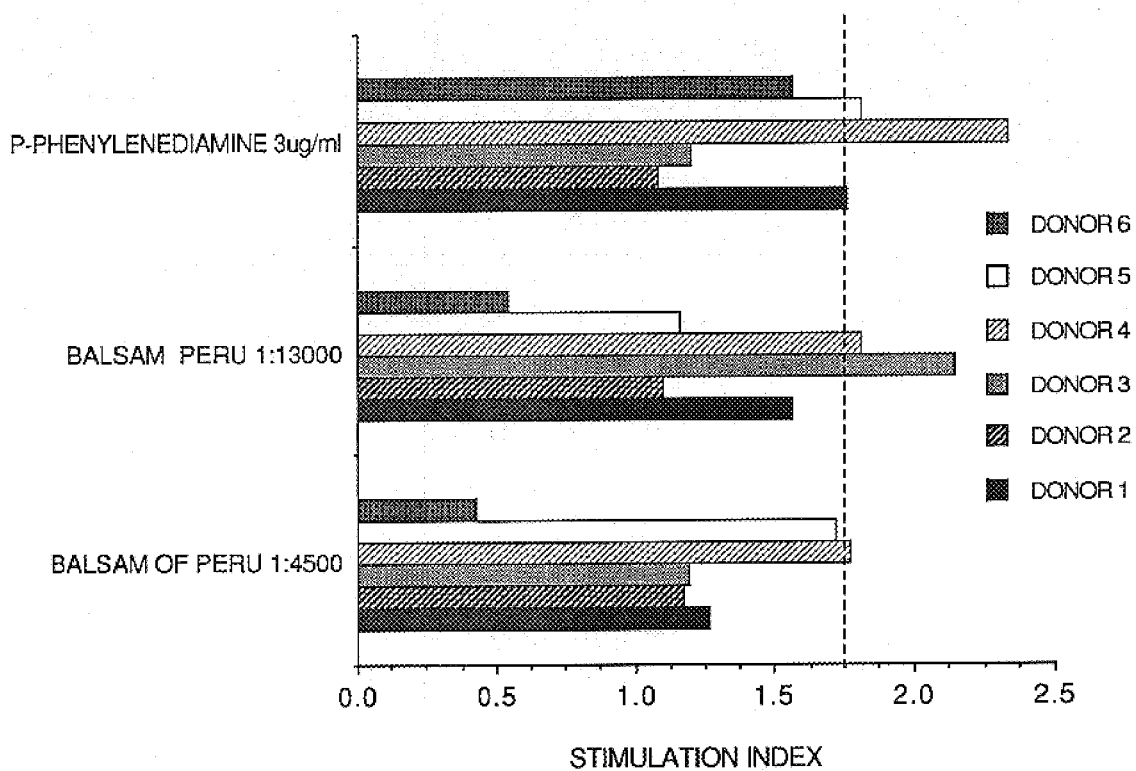

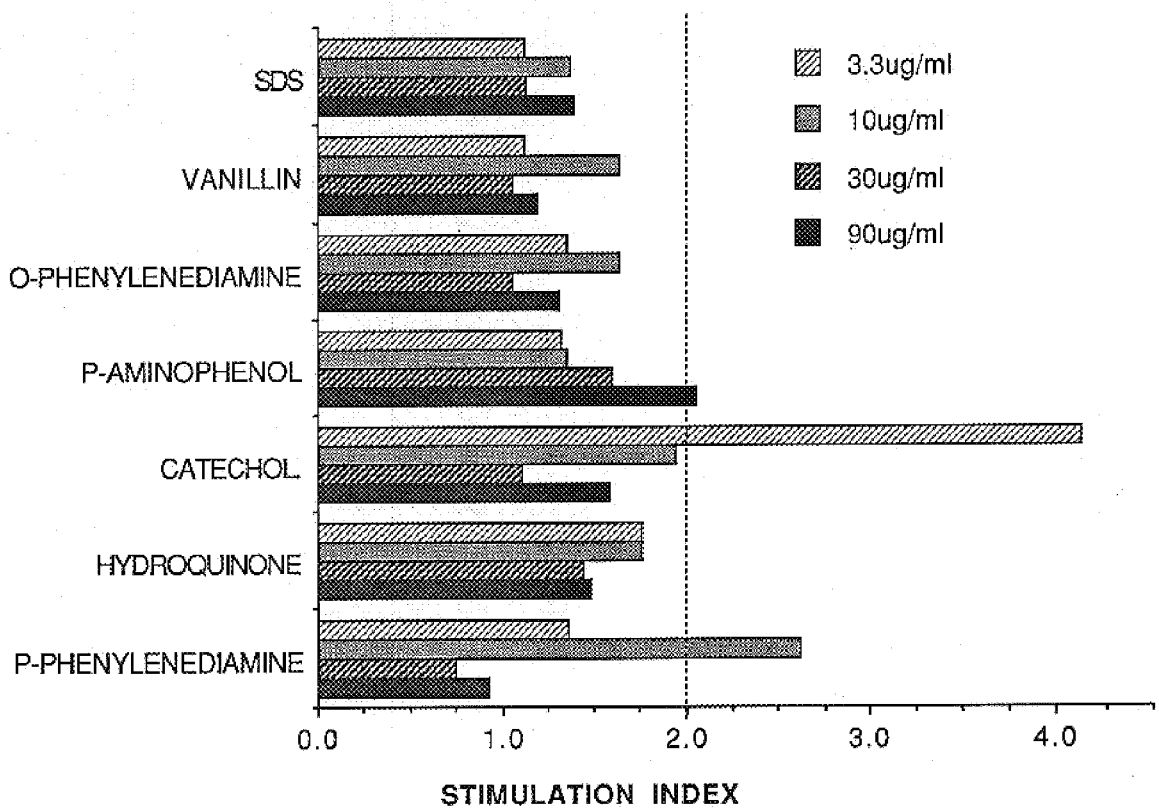

IDENTIFICATION OF HUMAN ALLERGENS AND T-LYMPHOCYTE ANTIGENS IN VITRO

FIELD OF THE INVENTION

The subject invention is directed generally to immunology, and more particularly to a method for screening a test compound for the ability of the test compound to induce a response from human naive T-cells, and to a method for primary in vitro sensitization of human naive T-cells.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

There is a great need for in vitro methods for testing allergenicity of compounds. This need is driven by socioeconomic factors related to concerns over animal testing. In particular, a method is needed to screen for potential allergens in products intended for topical application, such as cosmetics, and toiletry products. Currently, testing of potential allergens is largely performed on human subjects at great expense (1). Unfortunately, even the most extensive clinical trials employing over 100 subjects are unlikely to detect severe allergic reactions that may occur in 1/1,000 persons. Yet these rare severe reactions may present a significant risk to the population, as well as a large legal liability to the manufacturer.

Significant progress has been made on the development of in vitro assays for irritancy (2). However, in vitro assays that can distinguish irritants from allergens have not yet been developed, despite an extensive effort funded by the Center for Alternatives to Animal Testing @ Johns Hopkins University (3). Most allergens are also either clinical or subclinical irritants which further complicates the development of an assay for allergenicity. Generally, both allergens and irritants evoke a similar cytokine profile (4).

Allergenicity of topically applied compounds can be manifest as allergic contact dermatitis, photoallergic dermatitis, or contact urticaria (5,6,7). Allergic contact dermatitis is mediated by T-lymphocytes, and is a variant of delayed hypersensitivity in which the primary antigen presenting cell is the Langerhans dendritic cell (8). Allergens thus function as antigens to induce a T-lymphocyte response.

Primary in vitro sensitization is the sensitization of naive T-lymphocytes to antigens which the donor has never encountered. Other investigators have been unable to achieve primary in vitro sensitization without the use of dendritic cells (9,10,11,12,13,14). The use of peripheral blood human dendritic cells to distinguish allergens from irritants has been previously suggested (15). Dendritic cells are difficult to isolate in significant numbers (16), which greatly limits their application to a commercial assay.

The ability of dendritic antigen presenting cells to induce a primary immune response to a novel antigen is probably a function of the high expression of co-stimulatory molecules by these cells. Presentation of antigen to T-lymphocytes involves the interactions of multiple molecules, and T-cell receptor occupancy is not sufficient to induce T-cell proliferation (17). The interaction of CD28 and B7-1 (CD80) or B7-2 (CD86) has been shown to deliver such an essential co-stimulatory signal to human (18,19) CD4+ and CD8+ (20) T-cells. However, B7/CD28 signalling alone is inadequate to explain the unique capabilities of dendritic cells (21). Other molecule pairs with a role in co-stimulation or signaling of T-cells include ICAM-1/LFA-1 (22), LFA-3/CD2 (23), CD40/CD40-ligand (24), and possibly Heat Stable antigen (25). These co-stimulatory molecules are expressed at high levels on dendritic antigen presenting cells, and probably explain the ability of these cells to induce a primary immune response.

Since compounds which are unable to induce a T-lymphocyte response would be unable to induce allergic contact dermatitis, an in vitro method which detects the ability of novel compounds to induce a T-lymphocyte response may thus function as a screening assay for contact allergens. Due to the difficulty in isolating significant numbers of dendritic cells, the use of such cells as antigen presenting cells for primary in vitro sensitization has limited practical applications. A need continues to exist for a practical in vitro method for testing allergenicity and for primary in vitro sensitization.

SUMMARY OF THE INVENTION

The subject invention addresses this need by providing for the addition of an immortalized B-cell line to a sensitization culture to enable a primary in vitro response to novel antigens. If the B-cell line is not derived from the same donor as the responding lymphocytes, there is a response against the foreign transplantation antigens of the B-cell line. Such an alloantigen response precludes detection of primary in vitro sensitization. Therefore, this response to transplantation antigens is avoided by using a B-cell line which lacks both the class I (HLA-DR) and class II (HLA-A,B,C) major histocompatibility antigens (MHC). T2 cells are a line of EBV transformed B-cells which have deleted the gene for class II major histocompatibility locus transplantation antigens, and also have very low expression of class I MHC transplantation antigens (26). Addition of mitomycin C treated T2 cells to primary in vitro sensitization cultures permitted the detection of T-lymphocyte responses to novel antigens (allergens). This culture system has the potential to detect the immunogenic potential of weak allergens such as Balsam of Peru, and does not react to irritants, such as sodium dodecyl sulfate (SDS). This technology thus provides for primary in vitro sensitization without the use of dendritic cells. This technology can be used to identify human allergens and haptens. It can also identify peptides, or epitopes recognized by human T-lymphocytes, which is useful for vaccine development.

More particularly, the subject invention provides a method for screening a test compound for the ability of the test compound to induce a response from human naive T-cells. The method comprises admixing human naive T cells, macrophages/monocytes, immortalized B cells lacking class I and class II major histocompatibility antigens, and a test compound; and determining whether the test compound induces a response from the human naive T cells.

The invention further provides a method for primary in vitro sensitization of human naive T-cells. The method comprises admixing human naive T cells, macrophages/monocytes, immortalized B cells lacking class I and class II major histocompatibility antigens, and an antigen.

BRIEF DESCRIPTION OF THE DRAWINGS

These and other features and advantages of this invention will be evident from the following detailed description of preferred embodiments when read in conjunction with the accompanying drawings in which:

FIG. 1: Peripheral blood mononuclear cells (PBMC), including lymphocytes and monocytes, were incubated in the presence or absence of mitomycin C treated T2 cells, and either paraphenylenediamine (3 μg/ml) or media alone for 6 days. $^3$H-thymidine was then added to the cultures for 18 hours and uptake was determined by scintillation counting. This experiment was performed simultaneously with PBMC from 4 donors. Only in the presence of T2 cells was there a response to the paraphenylenediamine;

FIG. 2: PBMC from 4 donors were incubated for 6 days with mitomycin C treated T2 cells and either media or chemicals as shown. (3/4) Donor PBMC responded to paraphenylenediamine. However, none of the donor PBMC responded to SDS (irritant) or vanillin (weak allergen);

FIG. 3: PBMC from 6 donors were incubated for 6 days with mitomycin C treated T2 cells and either media or chemicals as shown. (3/6) Donor PBMC responded to paraphenylenediamine, and (3/6) donor PBMC responded to Balsam of Peru; and FIG. 4: PBMC were incubated 6 days with mitomycin C treated T2 cells and either media or test compounds as shown. In this experiment, a positive response was seen to paraphenylenediamine, catechol, and p-aminophenol. The irritant Sodium dodecyl sulfate (SDS) gave a negative response, as did the weak allergen vanillin.

DETAILED DESCRIPTION OF THE INVENTION

The subject invention provides a method for screening a test compound for the ability of the test compound to induce a response from human naive T-cells. The method comprises admixing human naive T cells, macrophages/monocytes, immortalized B cells lacking class I and class II major histocompatibility antigens, and a test compound; and determining whether the test compound induces a response from the human naive T cells.

The method of the subject invention can be used to screen any test compound to determine whether the test compound induces a response from human naive T cells. A response will be detected if the human naive T cells are capable of recognizing the particular test compound through their specific receptors. The types of test compounds which one may wish to screen using the method of the subject invention are many. In one embodiment, the response is an allergic response and the test compound is an allergen. Such allergens of interest include components of products intended for topical application, such as cosmetics, and toiletry products. Botanically derived fragrances, such as balsam of peru, are commonly used in various products intended for human use and newly discovered fragrance sources need to be screened for allergenicity. This screening is readily accomplished using the method of the subject invention.

In a further embodiment, the test compound may be an antigen. Antigens encoded by infectious agents such as viruses, microorganisms and their products, as well as tumor antigens expressed by cancer cells, can be screened according to the subject method. The types of antigens are numerous, and include, for example, a bacterial antigen, a viral antigen, a fungal antigen, a blood group antigen, a tumor cell-specific antigen, a tumor-associated antigen, and a parasitic antigen. Exemplary bacterial antigens include Staphylococcal antigens, Mycobacterial antigens, or *Borrelia burgdorferi* antigens. Exemplary viral antigens include those from the viruses human immunodeficiency virus, hepatitis virus, cytomegalovirus, herpes simplex virus, and varicella zoster virus. For example, the virus may be human immunodeficiency virus and the viral antigen may be gp160. Antigens may be screened as purified naturally occurring whole polypeptides, whole organisms or cells in viable or dead forms, protein fragments generated by enzymatic digestion, or synthetic peptides produced by solid phase chemical methods.

The test compound may also be a hapten or prohapten, such as paraphenylenediamine, M-phenylenediamine, O-phenylenediamine, P-aminophenol, M-aminophenol, or other dye compounds. The test compound may also be a peptide, or a drug, including drugs administered systemically (for example, orally, intravenously, intramuscularly, and sub-cutaneously), topically, or transdermally.

Preferably, the immortalized B cells are T2 cells and are immortalized using Epstein Barr virus. The immortalized B cells may be treated prior to admixing to prevent their proliferation. Suitable treatments include treatment with mitomycin C, treatment with paraformaldehyde, or treatment with radiation.

The human naive T cells and the macrophages/monocytes may be provided as a sample of human peripheral blood mononuclear cells derived from human blood, which may be provided as a panel of cells from separate donors. The human naive T cells and the macrophages/monocytes may also be provided as a human blood sample.

The determination of whether the test compound induces a response from the human naive T cells can be done with any suitable method. The determination may involve measuring for proliferation of the human naive T cells. This can be accomplished by radioactively labeling the human naive T cells (for example, with $^3$H-thymidine) and measuring radioactivity. Alternative or additionally, the determination of induction of a response may involve measuring for cytokine production by the human naive T cells. This can be done using analysis by enzyme-linked immunosorbent assay.

The subject invention further provides a method for primary in vitro sensitization of human naive T-cells. The method comprises admixing human naive T cells, macrophages/monocytes, immortalized B cells lacking class I and class II major histocompatibility antigens, and an antigen. In one embodiment, the antigen is an allergen. Suitable allergens include botanically derived fragrances such as balsam of peru. The antigen may also be a bacterial antigen (for example, a Staphylococcal antigen, a Mycobacterial antigen, or a *Borrelia burgdorferi* antigen), a viral antigen (for example, from human immunodeficiency virus, hepatitis virus, cytomegalovirus, herpes simplex virus, or varicella zoster virus), a fungal antigen, a blood group antigen, a tumor cell-specific antigen, a tumor-associated antigen, or a parasitic antigen. In one embodiment, the virus is human immunodeficiency virus and the viral antigen is gp160.

The antigen may also be a hapten or prohapten, such as paraphenylenediamine, M-phenylenediamine, O-phenylenediamine, P-aminophenol, M-aminophenol, or other dye compounds. The antigen may also be a peptide, or a drug, including drugs administered systemically (for example, orally, intravenously, intramuscularly, and sub-cutaneously), topically, or transdermally.

Preferably, the immortalized B cells are T2 cells and are immortalized using Epstein Barr virus. The immortalized B cells may be treated prior to admixing to prevent their proliferation. Suitable treatments include treatment with mitomycin C, treatment with paraformaldehyde, or treatment with radiation.

The human naive T cells and the macrophages/monocytes may be provided as a sample of human peripheral blood mononuclear cells derived from human blood, which may be provided as a panel of cells from separate donors. The human naive T cells and the macrophages/monocytes may also be provided as a human blood sample.

To summarize the subject invention, primary in vitro sensitization is the sensitization of naive T-lymphocytes to antigens which the donor has never encountered. The ability of a compound to sensitize T-lymphocytes can be used as an in vitro assay for allergenicity or immunogenicity. Other investigators have been unable to achieve primary in vitro sensitization without the use of dendritic cells, which are difficult to isolate in significant numbers. One unique aspect of this technology is primary in vitro sensitization without the use of dendritic cells. This is achieved, in one embodiment, by adding Epstein Barr virus (EBV) transformed human B-cells as a source of co-stimulatory molecules. The human B-cell line used as a source of co-stimulatory molecules lacks the major histocompatibility transplantation antigens HLA-DR, and HLA-A,B,C. This permits the use of these B-cells with lymphocytes from unrelated donors. The B-cells may be mitomycin C treated to prevent proliferation. Culture of these co-stimulatory B-cells lacking transplantation antigens, with human lymphocytes, monocytes, and allergen, induces primary in vitro sensitization of T-lymphocytes to the allergen. Peripheral blood monocytes function as antigen presenting cells in this system, since the co-stimulatory B-cells lack antigen presenting molecules. Sensitization can be detected as $^3$H-thymidine uptake by T-lymphocytes. This culture system can detect sensitization to weak and moderate human contact allergens, as well as peptides, and can function as an in vitro screen for allergenic compounds, or immunogenic peptides.

Methods

Preparation of peripheral blood mononuclear cells (PBMC). The research protocol was approved by the Committee on Research Involving Human Subjects of SUNY @ Stony Brook. After informed consent, heparinized blood was obtained by venipuncture. PBMC (peripheral blood mononuclear cells, which include lymphocytes and macrophages/monocytes) were prepared from heparinized peripheral blood by density centrifugation over Ficoll/Hypaque (Pharmacia, Piscataway, N.J.). PBMC were then washed 3 times in serum free wash medium consisting of SMEM (Gibco, Grand Island, N.Y.), and mixed (1:1) with AIM V medium (Gibco). At no time did the PBMC contact animal serum. PBMC were counted, and resuspended at $2\times10^6$ cells/ml in AIM V medium (Gibco).

T2 cells. T2 cells (Atec Accession No. CRL-1992) are a human derived B-cell line which is deficient in it's expression of both class I (HLA-A,B,C), and class II (HLA-DR) major histocompatibility complex (MHC) antigens. This deficiency results from a deletion of the TAP transporter genes which transport peptides into the endoplasmic reticulum for presentation by the MHC class I molecules (27,28). This deletion also encompasses the HLA-DR gene. The cell line was obtained from Dr. Peter Cresswell (Yale Medical School, New Haven, Conn.).

Preparation and mitomycin C treatment of T2 cells. T2 cells were cultured in AIM V media (Gibco). Prior to treatment, they were washed, counted, and resuspended in AIM V media at $2\times10^6$ cells/ml. Mitomycin C (Sigma, St Louis, Mo.) was then added at 30 μg/ml for a 2 hour incubation at 37° C. The T2 cells were then washed 4 times in serum free wash media, counted with trypan blue dye exclusion, and resuspended at $1\times10^6$ cells/ml.

Balsam of Peru. This common ingredient of fragrance mixes is present in a large variety of consumer products, including perfumes, moisturizers, cosmetics, and toiletries, and is a significant cause of allergic contact dermatitis to these products (29,30,31). Components of Balsam of Peru include cinnamic acid, cinnamic aldehyde, cinnamic alcohol, vanillin, and eugenol (32).

Paraphenylenediamine. Paraphenylenediamine (Aldrich, Milwaukee, Wis.) is used in oxidative hair dyes, and is the primary cause of allergic contact dermatitis to permanent hair dyes (33). It is also used as a dye for leather, and fur, as well as an anti-oxidant oil additive. Allergy to paraphenylenediamine may be mediated by its' oxidative product, Brandrowski's base (34).

HIV virus derived peptide P18. The HIV peptide chosen for these studies is an epitope originally defined by recognition by class I MHC restricted CD8+ T-cells of Balb/c H-$2^d$ mice (35). This 15mer peptide, referred to as P18, corresponds to residues 315–329 of gp160. It over-laps a major hypervariable B-cell epitope associated with virus neutralization. Recognition of peptide P18 by human cytotoxic CD8+ cells is restricted by HLA-A2, A3 and A11 (36). P18 peptide also induces it's own CD4+help for P18 specific CD8+ cells indicating it has an epitope restricted by human MHC class II (37). The 15mer peptide was synthesized at the peptide synthesis facility of the University of Minnesota.

Purification of T-lymphocytes. Sheep erythrocyte receptor positive (E+) T-cells and negative (E−) non-T-cells were isolated by rosetting followed by centrifugation over a Ficoll-Hypaque gradient and lysis of sheep erythrocytes by ammonium chloride as described (38). The (E+) population was greater than 95% CD3+ as determined by cytofluorgraph analysis (below).

In vitro sensitization cultures. Cell cultures were performed in 96 well U-bottom trays (Linbro), with a total volume of 0.2 ml/well of AIM V medium (Gibco). PBMC ($2\times10^6$/ml) were first admixed with equal volumes of T2 cells ($1\times10^6$/ml), and 0.1 ml of the cell mixture was added to each well. Test compounds were then added (0.1 ml/well) at twice the desired final concentration. Each well contained $1\times10^5$ PBMC, $5\times10^4$ T2 cells, and the test compound. Control wells contained 0.1 ml of media rather than test compound. The final ratio of PBMC to T2 cells was 2:1. There were 6 replicate wells per group. The 96-well trays were then cultured for 6 days at 37° C. in a 7.5% $Co_2$ incubator. After 6 days, 1 μCi of $^3$H-thymidine was added to each well. The wells were harvested 18 hours later, and $^3$H-thymidine uptake was determined with a scintillation counter (Pharmacia LKB Nuclear, Gaithersburg, Md.).

Cytofluorograph analysis of cell phenotype. Cells were phenotyped following immunofluorescence staining with anti-HLA-DR (L243; ATCC, Rockville, Md.), anti-HLA-A, B,C (W6/32; ATCC), anti-CD80 (B7-1, IgM; Ancell, Bayport, Minn.), anti-CD86 (B7-2, $IgG_1$; Ancell, Bayport, Minn.), anti-CD54 (ICAM-1, $IgG_1$; AMAC Inc, Westbrook, Me.), and anti-CD3 (RW2-8C8, $IgG_1$; Dr. Chikao Morimoto, Dana-Farber Cancer Institute, Boston, Mass.), followed by goat anti-mouse FITC (Sigma, St. Louis, Mo.). Mouse $IgG_1$ and mouse IgM (Sigma, St Louis, Mo.) were used as negative controls, as appropriate. The analysis was performed by the flow cytometry facility at SUNY Stony Brook using a FACSTAR PLUS. Non-viable cells were gated out by forward and side-scatter.

EXAMPLE I

Admixture of T2 Cells and PBMC Allows a Primary in vitro Response to Contact Allergens and HIV Derived Peptides.

Under standard culture conditions, PBMC do not respond in in vitro proliferation assays to antigens which the donor had not been previously sensitized to. This is because macrophages and monocytes are unable to induce a primary immune response (9). Such primary in vitro sensitization can be achieved with the use of dendritic antigen presenting cells. The subject invention makes use of the discovered fact that human B-cell lines can provide the necessary co-stimulatory molecules needed for primary in vitro sensitization, thereby avoiding the requirement for dendritic antigen presenting cells. A B-cell line deficient in HLA-A, B,C (MHC class I) and HLA-DR (MHC class II) antigens has an advantage, in that it may be used as a source of co-stimulation for allogeneic PBMC. T2 cells are such a human B-cell line, which is deficient in both MHC class I and class II antigens.

The ability of T2 cells to provide the co-stimulatory signals needed for a primary in vitro sensitization response was tested. PBMC were obtained from a donor who had no previous contact with either the HIV virus (HIV negative by serum ELISA), or paraphenylenediamine. These PBMC were cultured with paraphenylenediamine 3 μg/ml, or HIV gp160 P18 peptide 10 μg/ml in the presence and absence of mitomycin C treated T2 cells. In the absence of T2 cells there was no response to either antigen. However, when PBMC were admixed with T2 cells at a ratio of 2:1 there was a statistically significant response to both paraphenylenediamine and HIV P18 peptide (Table 1). This requirement for T2 cells to induce a response of naive PBMC to paraphenylenediamine was confirmed with 4 additional donors (FIG. 1). Since the T2 cells lack the HLA-DR, and HLA-A,B,C antigen presenting molecules, it is likely that monocytes function as antigen presenting cells in this system. Thus, the T2 cells have a role in supplying co-stimulatory molecules, but are not functioning as antigen presenting cells.

EXAMPLE II
Phenotype of T2 Cells.

T2 cells were phenotyped by immunofluorescence staining and cytofluorograph analysis. As reported, the T2 cells did not express detectable HLA-DR, or HLA-A,B,C. The T2 cells did express the co-stimulation molecules B7-1 (CD80), and B7-2 (CD86), as well as the adhesion molecule ICAM-1 (CD54).

EXAMPLE III
In vitro Sensitization Induced by T2 Cells is Mediated by T-cells, and is Dependent Upon non-T Cells to Present Antigen.

Lymphocyte proliferation assays are generally the result of T-lymphocyte proliferation. It was confirmed that this was also true of this novel in vitro sensitization system. T-cells (70%) were mixed with irradiated (6,000R) non-T cells (30%) for a test of in vitro sensitization to paraphenylenediamine in the presence of mitomycin C treated T2 cells. In a reciprocal group, non-T cells (70%) were mixed with irradiated T-cells (30%). These cell mixtures were added to the culture system, admixed with mitomycin C treated T2 cells, and paraphenylenediamine. Response to paraphenylenediamine was only detected in the groups with non-irradiated T-cells, there was no response in the group where the T-cells had been irradiated (Table 2). This indicates that the response to antigen in this in vitro sensitization system is mediated by T-cells. T-cells admixed with T2 cells in the absence of non-T cells gave no response, indicating that the T2 cells are not sufficient for antigen presentation, and autologous non-T cells (e.g. monocytes, macrophages) are required. The T2 cells are not functioning as antigen presenting cells (which is to be expected since the T2 cells lack antigen presenting Major Histocompatibility Complex antigens HLA-DR and HLA-A,B,C), but rather function as accessory cells.

EXAMPLE IV
Primary in vitro Sensitization and Proliferation of PBMC to Compounds Correlated With Allergenicity.

It was proposed that only compounds with a potential for inducing an immune response would induce in vitro primary sensitization, and that this system may be useful for screening for contact allergens. Cultures were established using the above conditions with admixed T2 cells, and a variety of test compounds. The compounds tested were paraphenylenediamine (moderate allergen), vanillin (weak allergen), and sodium dodecyl sulfate (SDS, Sigma; irritant). Each compound was tested from 3.3 μM to 60 μM. Of the 4 donors shown, 3 responded to paraphenylenediamine, and none responded to either vanillin or SDS (FIG. 2). This response was able to differentiate irritants from allergens. Additional experiments demonstrated a response to the commercially important fragrance allergen Balsam of Peru in 3/6 donors (FIG. 3), as well as the contact allergens p-aminophenol and catechol (FIG. 4).

EXAMPLE V

It was possible to sensitize naive human T-lymphocytes to allergens (antigens) in vitro by the use of an accessory cell expressing co-stimulatory molecules. These accessory T2 cells lacked the major transplantation antigens HLA-DR, and HLA-A,B,C, and it was possible to use the T2 cells in culture with lymphocytes from unrelated donors. Monocytes and macrophages are unable to induce a primary in vitro immune response of naive T-lymphocytes (9), and the accessory T2 cells were essential in obtaining a response. With these culture conditions, it was possible to induce a response to weak contact allergens, such as Balsam of Peru. However, the irritant sodium dodecyl sulfate did not induce a response. Thus, this culture system has the potential to both detect weak allergens and to distinguish irritants from allergens.

The subject invention uses EBV transformed B-cells lacking transplantation antigens as an additional source of co-stimulation for primary in vitro sensitization. The T2 cells in these sensitization cultures do not present the antigen, because the T2 cells lack MHC molecules necessary for antigen presentation. Thus, the T2 cells do not act as antigen presenting cells, but as co-stimulatory cells, which enable primary in vitro sensitization.

This sensitization technique could also be used to detect allergenicity of drugs intended for systemic administration. Most drugs are prohaptens, which are metabolically activated to a reactive intermediate that covalently binds proteins (39). The application of this in vitro sensitization system for prediction of drug allergenicity would require the addition of an in vitro metabolic activation step for the drugs, such as has been reported with the use of liver microsomes (40).

Allergic contact dermatitis is initiated by presentation of allergens or haptens by Langerhans cells, a form of dendritic antigen presenting cell. Mouse (41) and human (42) Langerhans cells are able to induce primary immune responses in vitro. Dendritic antigen presenting cells isolated from the peripheral blood of humans can also induce a primary in vitro immune response (9,10,11,43,44). It is possible to culture and expand these dendritic cells with the use of cytokines including GM-CSF (16,45,46,47). These cultured dendritic antigen presenting cells can also induce a primary in vitro immune response, and their use in predictive testing for allergenicity has been proposed (11).

This technique for primary in vitro sensitization of T-lymphocytes differs from the previously described techniques, in that it does not make use of Langerhans cells or other dendritic antigen presenting cells. The use of a co-stimulatory cell line lacking transplantation antigens is unique. It was demonstrated that this culture system has the ability to recognize weak allergens, such as Balsam of Peru, and to distinguish them from irritants, such as SDS. The ability of this culture system to screen for potential allergens fills a great need.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

CONDITIONS FOR PRIMARY IN VITRO SENSITIZATION
PARAPHENYLENEDIAMINE, HIV gp160 15mer
USE OF MITOMYCIN C TREATED T2 CELLS;
VARY CELL NUMBERS

| SAMPLE | | MEAN dpm | SEM | S.I.[a] |
|---|---|---|---|---|
| PBMC 1 × 10⁵/well; no T2 cells | | | | |
| 1 MEDIA | | 2976[b] | 420 | REFERENCE |
| 2 PARAPHENYLENEDIAMINE | 3 µg/ml | 2869 | 653 | 0.96 |
| 3 gp160 15mer PEPTIDE | 10 µg/ml | 3509 | 264 | 1.18 |
| PBMC at 1 × 10⁵/well; T2 cells at 5 × 10⁴/well | | | | |
| 4 MEDIA | | 3512 | 546 | REFERENCE |
| 5 PARAPHENYLENEDIAMINE | 3 µg/ml | 6935 | 790 | 1.97[c] |
| 6 gp160 15mer PEPTIDE | 10 µg/ml | 11366 | 865 | 3.24[c] |
| PBMC at 1 × 10⁵/well; T2 cells at 1 × 10⁵/well | | | | |
| 7 MEDIA | | 7027 | 698 | REFERENCE |
| 8 PARAPHENYLENEDIAMINE | 3 µg/ml | 7856 | 793 | 1.12 |
| 9 gp160 15mer PEPTIDE | 10 µg/ml | 5113 | 602 | 0.73 |

³H-thymidine uptake of cultured PBMC in the presence, and absence of T2 cells at the indicated numbers per well.
[a]Stimulation index: response to antigen/response to media
[b]Mean ³H-thymidine uptake of 6 replicate wells
[c]$p < 0.01$ by T-test relative to media (group 4)

TABLE 2

IN VITRO SENSITIZATION INDUCED BY T2 CELLS IS
MEDIATED BY T-CELLS, AND DEPENDENT UPON NON-T
CELLS TO PRESENT ANTIGEN

| ANTIGEN | RESPONDERS | MEAN[a] | SEM | S.I.[b] |
|---|---|---|---|---|
| MEDIA | PBMC; NO T2 CELLS[c] | 2973 | 280 | REFERENCE |
| P-PD[d] | PBMC; NO T2 CELLS | 3054 | 635 | 1.03 |
| MEDIA | PBMC + T2 CELLS | 5741 | 734 | REFERENCE |
| P-PD | PBMC + T2 CELLS | 11973 | 813 | 2.09[e] |

TABLE 2-continued

IN VITRO SENSITIZATION INDUCED BY T2 CELLS IS
MEDIATED BY T-CELLS, AND DEPENDENT UPON NON-T
CELLS TO PRESENT ANTIGEN

| ANTIGEN | T-CELLS | NON-T CELLS | T2 CELLS | MEAN/SEM | S.I. |
|---|---|---|---|---|---|
| MEDIA | YES | NO | YES | 3387/318 | REFERENCE |
| P-PD | YES | NO | YES | 2263/317 | 0.67 |
| MEDIA | 70% | 30% (6,000R) | YES | 25858/1560 | REFERENCE |
| P-PD | 70% | 30% (6,000R) | YES | 50220/2643 | 1.94[e] |
| MEDIA | 30% (6,000R) | 70% | YES | 5465/847 | REFERENCE |
| P-PD | 30% (6,000R) | 70% | YES | 3096/446 | 0.57 |

[a]Mean ³H-thymidine uptake of 6 replicate wells
[b]Stimulation index: response to antigen/response to media
[c]T2 cells were treated with mitomycin C
[d]P-PD: paraphenylenediamine 10 µg/ml
[e]$p < 0.001$ by T-test relative to respective reference group References 1. Ippen M D, Cosmetic Dermatology (Suppl) 8:17–19, 1996.
2. Narvell J, et al., Clinical Toxicology 30:359–369, 1992.
3. Elmets C A, In Vitro Toxicology 9:223–235, 1996.
4. Eun H C, Jung S Y, Contact Derm 30:168–171, 1994
5. Adams R M, Maibach H I, J Am Acad Dermatol 13:1062–1069, 1985.
6. Rietschel R L, Fowler J F, In: *Fisher's Contact Dermatitis*, Fourth Edition, Williams & Wilkins, Philadelphia, 1995, pp257–329.
7. de Groot A C, et al., Contact Dermatitis 19:195–201, 1988.
8. Kalish R S, Arch Dermatol 127:1558–1563, 1991.
9. Mehta-Damani A, et al., Source Euro J Immunol 25:1206–1211, 1995.
10. Mehta-Damani A, et al., J Immunol 153:996–1003, 1994.
11. Degwert J, et al., Adv Exper Med Biol 378:187–189, 1995.
12. Moulon C, et al., Adv Exper Med Biol 329:209–212, 1993.
13. Fagnoni F F, et al., Immunology 85:467–474, 1995.
14. Hsu F J, et al., Nature Med 2:52–58, 1996.
15. Degwert J, et al., Abstract P-84, American Academy of Dermatology Annual Meeting, Feb. 10–15, 1996, Washington D.C., USA.
16. Markowicz S, Engleman E G, J Clin Invest 85:955–961, 1990.
17. Jenkins M K, Schwartz R H, J Exp Med 165:302–319, 1987.
18. Jenkins M K, et al., J Immunol 147:2461–2466, 1991.
19. Young J W, et al., J Clin Invest 90:229–237, 1992.
20. Kalish R S, Wood J A, J Invest Dermatol 108:253–257, 1997.
21. Fagnoni F F, et al., Immunology 85:467–474, 1995.
22. Boyd A W, et al., Proc Natl Acad Sci USA 85:3095–3099, 1988.
23. Bohmig G A, et al., J Immunol 152:3720–3728, 1994.
24. Wu Y, et al., Current Biol 5:1303–11, 1995.
25. Enk A H, Katz S I, J Immunol 152:3264–3270, 1994.
26. Riberdy J M, Cresswell P, J Immunol 148:2586–2590, 1992.
27. Wei M L, Cresswell P, Nature (Lond.) 356:443–446, 1992.

28. Crumpacker D B, et al., J Immunol 148:3004–3011, 1992.
29. Edman B, Contact Dermatitis 31:291–2, 1994.
30. Bruckner-Tuderman L, et al., Dermatology 184:29–33, 1992.
31. Fisher A A, Cutis 45:21–3, 1990.
32. Hjorth, N, *Eczematous allergy to balsams, allied perfumes and flavoring agents*, Copenhagen, Munksgaard, 1961, pp134.
33. Marcoux D, Riboulet-Delmas G, American Journal of Contact Dermatitis 5:123–129, 1994.
34. Krasteva M, et al., International Archives Allergy Immunology 102:200–4, 1993.
35. Takahashi H, et al., Proc Natl Acad Sci USA 85:3105–3109, 1988.
36. Achour A, et al., AIDS Res & Human Retroviruses 10:19–25, 1994.
37. Takahashi H, et al., J Exp Med 171:571–576, 1990.
38. Kalish R S, et al., Cell Immunol 111:379–389, 1988.
39. Shear N H, et al., Ann Intern Med 105:179–184, 1986.
40. Spielberg S P, Fed Proc 43:2308–2313, 1984.
41. Hauser C, Katz S I, Proc Natl Acad Sci USA 85:5625–5628, 1988.
42. Moulon C, et al., Immunology 80:373–379, 1993.
43. Engleman E, et al., METHODS FOR USING DENDRITIC CELLS TO ACTIVATE T CELLS, PCT International Publication No. WO 94/02156, published Feb. 3, 1994.
44. Engleman E, et al., METHODS FOR IN VIVO T CELL ACTIVATION BY ANTIGEN-PULSED DENDRITIC CELLS, PCT International Publication No. WO 95/34638, published Dec. 21, 1995.
45. Strunk D, et al., Blood 87:1292–1302, 1996.
46. Bernhard H, et al., Cancer Research 55:1099–1104, 1995.
47. Sallusto F, Lanzavecchia A, J Exp Med 179:1109–1118, 1994.

What is claimed is:

1. A method for screening a test compound for the ability of the test compound to induce a response from human naive T-cells, the method comprising:
   obtaining a sample of human blood, wherein the sample of human blood contains human naive T cells and macrophages/monocytes;
   admixing the sample of human blood with immortalized B cells lacking class I and class II major histocompatibility antigens and with a test compound, wherein the B cells act as co-stimulatory molecules; and
   determining whether the test compound induces a response from the human naive T cells.
2. The method of claim 1 wherein the test compound is an allergen.
3. The method of claim 2 wherein the allergen is a botanically derived fragrance.
4. The method of claim 3 wherein the botanically derived fragrance is balsam of peru.
5. The method of claim 1 wherein the test compound is an antigen.
6. The method of claim 5 wherein the antigen is selected from the group consisting of a bacterial antigen, a viral antigen, a fungal antigen, a blood group antigen, a tumor cell-specific antigen, a tumor-associated antigen, and a parasitic antigen.
7. The method of claim 6 wherein the bacterial antigen is a Staphylococcal antigen, a Mycobacterial antigen, or a *Borrelia burgdorferi* antigen.
8. The method of claim 6 wherein the viral antigen is from a virus selected from the group consisting of human immunodeficiency virus, hepatitis virus, cytomegalovirus, herpes simplex virus, and varicella zoster virus.
9. The method of claim 8 wherein the virus is human immunodeficiency virus and the viral antigen is gp160.
10. The method of claim 1 wherein the test compound is a hapten or prohapten.
11. The method of claim 10 wherein the test compound is a prohapten.
12. The method of claim 10 wherein the test compound is selected from the group consisting of paraphenylenediamine, M-phenylenediamine, O-phenylenediamine, P-aminophenol, M-aminophenol, and other dye compounds.
13. The method of claim 1 wherein the test compound is a peptide.
14. The method of claim 1 wherein the test compound is a drug.
15. The method of claim 1 wherein the immortalized B cells are T2 cells.
16. The method of claim 1 wherein the immortalized B cells are immortalized using Epstein Barr virus.
17. The method of claim 1 wherein the immortalized B cells are treated prior to admixing to prevent their proliferation.
18. The method of claim 17 wherein the immortalized B cells are treated with mitomycin C.
19. The method of claim 17 wherein the immortalized B cells are treated with paraformaldehyde.
20. The method of claim 17 wherein the immortalized B cells are treated with radiation.
21. The method of claim 1 wherein the sample of human blood is provided as a panel of blood samples from separate donors.
22. The method of claim 1 wherein determining whether the test compound induces a response from the human naive T cells comprises measuring for proliferation of the human naive T cells.
23. The method of claim 22 wherein measuring for proliferation of the human naive T cells comprises radioactively labeling the human naive T cells and measuring radioactivity.
24. The method of claim 23 wherein radioactively labeling the human naive T cells comprises labeling the human naive T cells with $^3$H-thymidine.
25. The method of claim 1 wherein determining whether the test compound induces a response from the human naive T cells comprises measuring for cytokine production by the human naive T cells.
26. The method of claim 25 wherein measuring for cytokine production by the human naive T cells comprises analysis by enzyme-linked immunosorbent assay.
27. A method for primary in vitro sensitization of human naive T-cells, the method comprising:
   obtaining a sample of human blood, wherein the sample of human blood contains human naive T cells and macrophages/monocytes; and
   admixing the sample of human blood with immortalized B cells lacking class I and class II major histocompatibility antigens and with an antigen, wherein the B cells act as co-stimulatory molecules.
28. The method of claim 27 wherein the antigen is an allergen.
29. The method of claim 28 wherein the allergen is a botanically derived fragrance.
30. The method of claim 29 wherein the botanically derived fragrance is balsam of peru.
31. The method of claim 27 wherein the antigen is selected from the group consisting of a bacterial antigen, a viral antigen, a fungal antigen, a blood group antigen, a tumor cell-specific antigen, a tumor-associated antigen, and a parasitic antigen.

32. The method of claim 31 herein the bacterial antigen is a Staphylococcal antigen, a Mycobacterial antigen, or a *Borrelia burgdorferi* antigen.

33. The method of claim 31 wherein the viral antigen is from a virus selected from the group consisting of human immunodeficiency virus, hepatitis virus, cytomegalovirus, herpes simplex virus, and varicella zoster virus.

34. The method of claim 33 wherein the virus is human immunodeficiency virus and the viral antigen is gp160.

35. The method of claim 27 wherein the antigen is a hapten or prohapten.

36. The method of claim 35 wherein the antigen is a prohapten.

37. The method of claim 36 wherein the antigen is selected from the group consisting of paraphenylenediamine, M-phenylenediamine, O-phenylenediamine, P-aminophenol, M-aminophenol, and other dye compounds.

38. The method of claim 27 wherein the antigen is a peptide.

39. The method of claim 27 wherein the antigen is a drug.

40. The method of claim 27 wherein the immortalized B cells are T2 cells.

41. The method of claim 27 wherein the immortalized B cells are immortalized using Epstein Barr virus.

42. The method of claim 27 wherein the immortalized B cells are treated prior to admixing to prevent their proliferation.

43. The method of claim 42 wherein the immortalized B cells are treated with mitomycin C.

44. The method of claim 42 wherein the immortalized B cells are treated with paraformaldehyde.

45. The method of claim 42 erein the immortalized B cells are treated with radiation.

46. The method of claim 37 wherein the sample of human blood is provided as a panel of blood samples from separate donors.

* * * * *